(12) United States Patent
Olson et al.

(10) Patent No.: US 9,986,999 B2
(45) Date of Patent: Jun. 5, 2018

(54) HIGH-STRENGTH MULTI-COMPONENT SUTURE

(71) Applicant: Teleflex Medical Incorporated, Research Triangle Park, NC (US)

(72) Inventors: James R. Olson, Norwich, CT (US); Jiunn-Yow Chen, Amherst, NH (US); Dean Dinsmore, New Ipswich, NH (US); Jeffrey Wallace, Saunderstown, RI (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 777 days.

(21) Appl. No.: 14/471,716

(22) Filed: Aug. 28, 2014

(65) Prior Publication Data

US 2015/0066080 A1    Mar. 5, 2015

Related U.S. Application Data (60) Provisional application No. 61/871,709, filed on Aug. 29, 2013.

(51) Int. Cl.
*A61B 17/06* (2006.01)
*B29C 47/00* (2006.01)
(Continued)

(52) U.S. Cl.
CPC ........ *A61B 17/06166* (2013.01); *A61B 90/92* (2016.02); *A61L 17/04* (2013.01);
(Continued)

(58) Field of Classification Search
CPC .............................. A61B 17/06166
See application file for complete search history.

(56) References Cited

U.S. PATENT DOCUMENTS

| 3,398,219 A | 8/1968 | Kelly et al. |
| 4,370,114 A | 1/1983 | Okamoto et al. |

(Continued)

FOREIGN PATENT DOCUMENTS

| CA | 2087903 A1 | 7/1993 |
| JP | 2010-110686 A | 5/2010 |

(Continued)

OTHER PUBLICATIONS

European Search Report issued in European Patent Application No. 14839555.1 dated Oct. 4, 2016.
(Continued)

*Primary Examiner* — Larry Thrower
(74) *Attorney, Agent, or Firm* — Baker & Hostetler LLP (57) ABSTRACT

A method for making an expanded, and optionally multi-component and/or colored PTFE monofilament is disclosed. The method includes forming a first paste by mixing a PTFE powder with a hydrocarbon solvent; forming an extrusion preform by pressing the first paste into a form; curing the extrusion preform by exposing the extrusion preform to a first temperature for a first time duration; forming a green monofilament by extruding the first paste through a die; expanding the green monofilament by exposing the green monofilament to a second temperature for a second time duration, the second time duration occurring after the first time duration; stretching the green monofilament substantially along a longitudinal axis of the green monofilament, the stretching the green monofilament occurring after the expanding the green monofilament; and sintering the green monofilament after the stretching the green monofilament. The method may include doing all or some of the expanding, stretching and sintering steps simultaneously.

15 Claims, 10 Drawing Sheets

(51) Int. Cl.

| | | |
|---|---|---|
| *B29C 47/88* | (2006.01) | |
| *A61L 17/04* | (2006.01) | |
| *B29C 47/06* | (2006.01) | |
| *D01D 5/247* | (2006.01) | |
| *D01D 10/02* | (2006.01) | |
| *D01F 6/12* | (2006.01) | |
| *D01F 8/10* | (2006.01) | |
| *A61B 90/92* | (2016.01) | |
| *B29K 27/18* | (2006.01) | |
| *B29K 105/00* | (2006.01) | |
| *B29K 105/24* | (2006.01) | |
| *B29L 31/00* | (2006.01) | |
| *B29C 47/94* | (2006.01) | |
| *B29C 35/10* | (2006.01) | |
| *A61B 17/00* | (2006.01) | |

(52) U.S. Cl.
CPC ...... *B29C 47/0014* (2013.01); *B29C 47/0016* (2013.01); *B29C 47/0038* (2013.01); *B29C 47/0057* (2013.01); *B29C 47/06* (2013.01); *B29C 47/8805* (2013.01); *D01D 5/247* (2013.01); *D01D 10/02* (2013.01); *D01F 6/12* (2013.01); *D01F 8/10* (2013.01); *A61B 2017/00964* (2013.01); *B29C 35/10* (2013.01); *B29C 47/062* (2013.01); *B29C 47/064* (2013.01); *B29C 47/94* (2013.01); *B29K 2027/18* (2013.01); *B29K 2105/007* (2013.01); *B29K 2105/246* (2013.01); *B29K 2105/251* (2013.01); *B29K 2223/0683* (2013.01); *B29L 2031/753* (2013.01)

(56) References Cited

U.S. PATENT DOCUMENTS

| | | | |
|---|---|---|---|
| 4,381,274 A | 4/1983 | Kessler et al. | |
| 4,482,516 A | 11/1984 | Bowman et al. | |
| 4,743,480 A | 5/1988 | Campbell et al. | |
| 5,007,922 A * | 4/1991 | Chen ................ | A61B 17/06004 606/228 |
| 5,024,797 A * | 6/1991 | Anderheggen ......... | D01F 6/765 264/143 |
| 5,162,074 A | 11/1992 | Hills | |
| 5,167,890 A | 12/1992 | Sasshofer et al. | |
| 5,227,109 A | 7/1993 | Allen, III et al. | |
| 5,281,475 A | 1/1994 | Hollenbaugh, Jr. et al. | |
| 5,288,552 A | 2/1994 | Hollenbaugh, Jr. et al. | |
| 5,344,297 A | 9/1994 | Hills | |
| 5,364,699 A | 11/1994 | Hollenbaugh, Jr. et al. | |
| 5,429,869 A | 7/1995 | McGregor et al. | |
| 5,462,781 A | 10/1995 | Zukowski | |
| 5,562,987 A | 10/1996 | Shimizu | |
| 5,686,033 A * | 11/1997 | Shimizu .................... | D01F 6/12 264/127 |
| 5,718,251 A | 2/1998 | Gray et al. | |
| 5,718,926 A | 2/1998 | Dambrine et al. | |
| 5,733,308 A | 3/1998 | Daugherty et al. | |
| 5,827,611 A | 10/1998 | Forbes | |
| 5,845,652 A | 12/1998 | Tseng et al. | |
| 5,848,600 A | 12/1998 | Bacino et al. | |
| 5,869,181 A | 2/1999 | Kent et al. | |
| 5,878,758 A | 3/1999 | Bacino et al. | |
| 5,888,651 A | 3/1999 | Hoyt et al. | |
| 6,238,605 B1 | 5/2001 | Wimmer | |
| 6,506,197 B1 | 1/2003 | Rollero et al. | |
| 6,551,353 B1 | 4/2003 | Baker et al. | |
| 6,767,498 B1 | 7/2004 | Talley, Jr. et al. | |
| 6,803,102 B1 | 10/2004 | Talley et al. | |
| 6,833,104 B2 | 12/2004 | Berger | |
| 6,861,142 B1 | 3/2005 | Wilkie et al. | |
| 6,977,231 B1 | 12/2005 | Matsuda | |
| 6,994,763 B2 | 2/2006 | Austin | |
| 7,371,253 B2 | 5/2008 | Leung et al. | |
| 7,445,843 B2 | 11/2008 | Lutz et al. | |
| 7,524,445 B2 | 4/2009 | Duran et al. | |
| 7,615,282 B2 | 11/2009 | Lutz et al. | |
| 7,736,576 B2 | 6/2010 | Walter | |
| 7,736,739 B2 | 6/2010 | Lutz et al. | |
| 7,737,060 B2 | 6/2010 | Strickler et al. | |
| 7,740,020 B2 | 6/2010 | Lutz et al. | |
| 7,857,829 B2 | 12/2010 | Kaplan et al. | |
| 7,871,425 B2 | 1/2011 | Jones et al. | |
| 8,038,712 B2 | 10/2011 | van der Burg et al. | |
| 8,048,111 B2 | 11/2011 | Lutz et al. | |
| 8,048,440 B2 | 11/2011 | Chang et al. | |
| 8,142,475 B2 | 3/2012 | Viola | |
| 8,262,694 B2 | 9/2012 | Widomski et al. | |
| 2001/0016625 A1 * | 8/2001 | Lahijani ................. | C08L 27/18 525/151 |
| 2002/0031628 A1 | 3/2002 | Zumbrum et al. | |
| 2003/0082323 A1 * | 5/2003 | Venditti .................. | B29C 47/54 428/36.9 |
| 2004/0267316 A1 | 12/2004 | Powell et al. | |
| 2005/0053783 A1 * | 3/2005 | Almeida Neto .......... | D01F 6/12 428/372 |
| 2006/0135995 A1 | 6/2006 | Ruff et al. | |
| 2006/0269754 A1 | 11/2006 | Hayashi et al. | |
| 2008/0021501 A1 | 1/2008 | Schmieding | |
| 2008/0086170 A1 | 4/2008 | Jones et al. | |
| 2008/0243183 A1 | 10/2008 | Miller et al. | |
| 2008/0272327 A1 * | 11/2008 | Almeida Neto ..... | A61C 15/041 252/8.84 |
| 2009/0012560 A1 | 1/2009 | Hunter et al. | |
| 2009/0032470 A1 | 2/2009 | Bacino et al. | |
| 2009/0099597 A1 | 4/2009 | Isse | |
| 2009/0105753 A1 | 4/2009 | Greenhalgh et al. | |
| 2009/0143819 A1 | 6/2009 | D'Agostino | |
| 2009/0151745 A1 | 6/2009 | Padinger et al. | |
| 2010/0298875 A1 | 11/2010 | Leung et al. | |
| 2010/0298876 A1 | 11/2010 | Leung et al. | |
| 2010/0318124 A1 | 12/2010 | Leung et al. | |
| 2011/0277249 A1 | 11/2011 | Abuzaina et al. | |
| 2011/0282386 A1 | 11/2011 | Friedrich et al. | |
| 2012/0109193 A1 | 5/2012 | Primavera et al. | |
| 2012/0116449 A1 | 5/2012 | Kirsch et al. | |
| 2012/0130406 A1 | 5/2012 | Odermatt et al. | |
| 2012/0136388 A1 | 5/2012 | Odermatt et al. | |
| 2012/0150194 A1 | 6/2012 | Odermatt et al. | |
| 2012/0179198 A1 | 7/2012 | Schmieding et al. | |
| 2012/0232588 A1 | 9/2012 | Stocchero et al. | |
| 2013/0123839 A1 | 5/2013 | Sargeant et al. | |

FOREIGN PATENT DOCUMENTS

| | | |
|---|---|---|
| WO | 1995001190 A1 | 1/1995 |
| WO | 1997024078 A1 | 7/1997 |
| WO | 2001012073 A1 | 2/2001 |
| WO | 2004030705 A2 | 4/2004 |
| WO | 2004/113050 A1 | 12/2004 |
| WO | 2007053866 A1 | 5/2007 |

OTHER PUBLICATIONS

Aybek et al. "Seven years' experience with suture annuloplasty for mitral valve repair" Surgery for acquired Cardiovascular Disease, 2006, 131, pp. 99-106.

Chandler-Temple et al. "Expanded poly(tetrafluoroethylene): from conception to biomedical devices" Chemistry in Australia, 2008, 75(8), pp. 3-6.

David et al. "Chordal replacement with polytetrafluoroethylene sutures for mitral valve repari: A 25-year experience" Journal of Thoracic and Cardiovascular Surgery, [available online Jun. 17, 2012], Corrected Proof.

Hertweck et al. "Tensile characteristics of PTFE sutures" Biomaterials, 1988, 9(5), pp. 457-459.

Hiruma et al. "Ion beam modification of ePTFE for improving the blood compatibility" Surface & Coatings Technology, 2011, 206, 905-910.

(56) References Cited

OTHER PUBLICATIONS

Joseph et al. "Randomised Controlled Trial to Evaluate the Efficacy of TachoComb H Patches in Controlling PTFE Suture-hole Bleeding" Eur J Vasc Endovasc Surg, 2004, 27, pp. 549-552.

Minatoya et al. "Pathologic aspects of polytetrafuoroethylene sutures in human heart" The Annals of Thoracic Surgery, 1996, 61(3), pp. 883-887.

International Search Report dated Nov. 28, 2014 for PCT/US2014/053118 filed Aug. 28, 2014.

* cited by examiner

HIGH-STRENGTH MULTI-COMPONENT SUTURE

CROSS-REFERENCE TO RELATED APPLICATIONS

This application claims priority to provisional US patent application entitled, High Strength Multi-Component Suture, filed Aug. 29, 2013, having Ser. No. 61/871,709, the disclosure of which is hereby incorporated by reference in its entirety.

TECHNICAL FIELD

This disclosure relates generally to surgical sutures and, more particularly, to a multi-component expanded polytetrafluoroethylene (PTFE) surgical suture.

BACKGROUND

Surgical sutures are known for binding body tissues together or binding medical appliances to body tissue. Various materials, including natural materials and synthetic materials, for example, may compose a surgical suture. Further, surgical sutures may include various structures, such as a monofilament structure or a multi-filament structure, for example.

Canadian Patent Publication 2,087,903 ("the '903 publication"), entitled "Multicolored Surgical Braid," purports to address the problem of non-uniform tensile stress distribution across a cross section of a surgical suture. The '903 publication describes a braided surgical suture with different types of braids that can be distinguished by different multicolored patterns. However, the braided structures described in the '903 publication may provide low tensile strength and may present external surface roughness and cross sectional non-uniformity characteristic of the braid pattern applied. Further, the braided sutures described in the '903 publication may include interstices between the braided fibers, which can trap and retain moisture prior to use.

U.S. Patent Publication 2013/0123839 ("the '839 publication"), entitled "Chemical Knots for Sutures," purports to address the problem of increasing knot profile with increasing knot security (i.e., resistance to loosening and/or slipping of the knot). The '839 publication describes surface activated surgical sutures capable of forming chemically bonded knots. Further, the '839 publication states that a first reactive group may be positioned on a first portion of the suture surface and a second complimentary reactive group may be positioned on a second portion of the suture surface, such that the first and second portions of the suture surface may come in contact and during the knot-tying process and form a chemical bond therebetween. However, the '839 publication does not describe how to make high tensile strength sutures, or sutures having a color pattern indicative of a characteristic of the suture.

U.S. Patent Publication 2011/0277249 ("the '249 publication"), entitled "Method of Producing Colored High-Strength Fibers," purports to address the problem of successfully dyeing polyolefins. The '249 publication describes a process for producing colored high-strength fibers of ultra-high-molecular-weight polyolefins by pretreating at least a portion of the high-strength fiber with at least one etching agent, prior to applying a dye to the etched fiber. However, the multi-step process for forming a fiber, etching the fiber, and then dyeing the fiber may be complex and expensive.

Accordingly, there is a need for an improved surgical suture having high tensile strength, low cost, and a multicolored pattern for identifying a characteristic of the suture.

SUMMARY

In one aspect, the disclosure describes a method for making an expanded PTFE monofilament. The method includes forming a first paste by mixing a PTFE powder with a hydrocarbon solvent, the first paste including less than about 16% of the hydrocarbon solvent by weight; curing the first paste by exposing the first paste to a first temperature for a first time duration; forming an extrusion preform by pressing the first paste into a form; forming a green monofilament by extruding the first paste through a die; expanding the green monofilament by exposing the green monofilament to a second temperature for a second time duration, the second time duration occurring after the first time duration; stretching the green monofilament substantially along a longitudinal axis of the green monofilament, the stretching the green monofilament occurring after the expanding the green monofilament; and sintering the green monofilament after the stretching the green monofilament.

In another aspect, the disclosure describes a monofilament. The monofilament including a plurality of expanded PTFE materials including a first PTFE material in contact with a second PTFE material along a first longitudinal interface of the monofilament, the first PTFE material defining a first outer surface of the monofilament, the second PTFE material defining a second outer surface of the monofilament, a color of the first PTFE material being different from a color of the second PTFE material.

DETAILED DESCRIPTION

Throughout the drawings, like reference numbers refer to like elements, unless otherwise specified.

Figure 1:
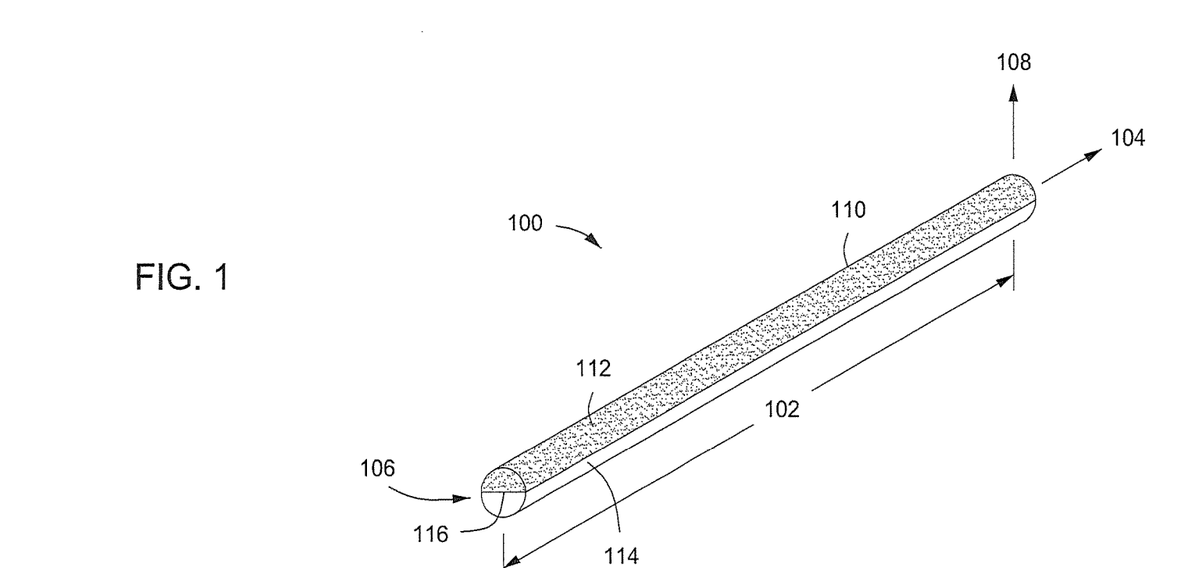
FIG. 1 shows a perspective view of a filament, according to an aspect of the disclosure.

FIG. 1 shows a perspective view of a filament 100, according to an aspect of the disclosure. The filament 100 has a length 102 that extends along a longitudinal axis 104, and a transverse profile 106 defined by cross section in a radial direction 108, where the radial direction 108 is perpendicular to the longitudinal axis 104. Although the filament 100 in FIG. 1 is shown with a monofilament structure, it will be appreciated that the filament 100 could also have a multi-filament structure. The filament 100 may be a surgical suture, or other filament structure known to persons having ordinary skill in the art.

A periphery of the transverse profile 106 of the filament 100 may be a generalized cylinder defined by an intersection of a plane extending in the radial direction 108 with an outer surface 110 of the filament 100. The generalized cylindrical cross section of the filament 100 could include a circular cross section, a polygonal cross section, an elliptical cross section, a lobed cross section, an irregular cross section, or other filament cross section known to persons having ordinary skill in the art. According to one aspect of the disclosure, the generalized cylindrical cross section of the filament 100 is substantially constant along the entire length 102 of the filament 100. Alternatively, according to another aspect of the disclosure, the transverse profile 106 of the filament 100 may vary along the longitudinal axis 104 of the filament 100.

The filament 100 includes a first composition 112 in contact with a second composition 114 along a longitudinal interface 116. The first composition 112 may differ from the second composition 114 by color, molecular weight, polymeric composition, bioactivity, or other suture material characteristic known to persons having ordinary skill in the art. According to one aspect of the disclosure, the first composition 112 differs from the second composition 114 only in color. According to another aspect of the disclosure, a color of first composition 112 is a natural color of a polymer composing at least a portion of the first composition 112. According to yet another aspect of the disclosure, a color of the first composition 112 is different from a natural color of a polymer composing at least a portion of the first composition 112.

The color of either the first composition 112 or the second composition 114 may be varied by addition of dyes, pigments, powders, or other colorants known to persons having ordinary skill in the art. A colorant may be either a dye or a pigment based on its solubility. Some inorganic pigments may be advantageous for coloring PTFE products because they provide high temperature resistance, for example, during sintering.

Figure 2:
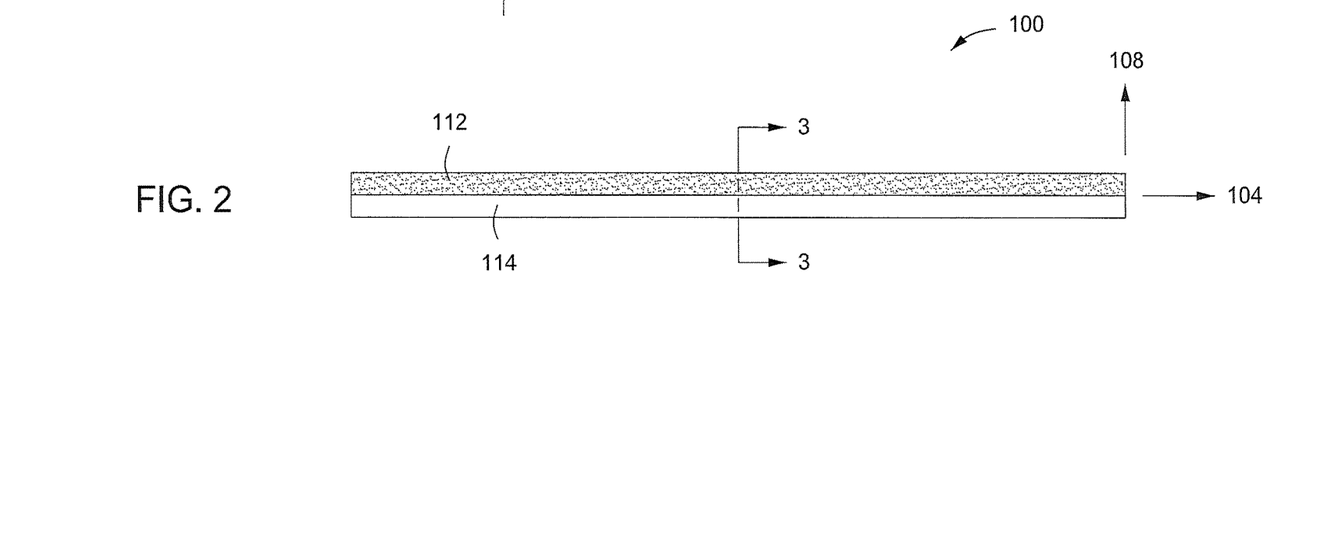
FIG. 2 shows a front view of the filament illustrated in FIG. 1.
Figure 3:
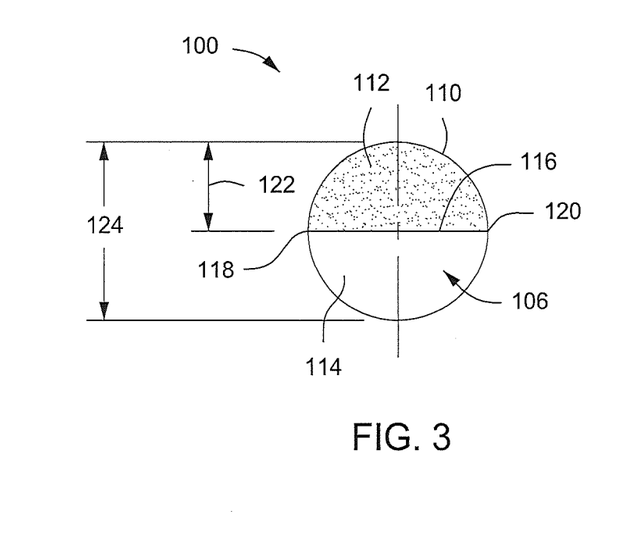
FIG. 3 shows a radial cross section of the filament in FIG. 2 along section 3-3.
Figure 4:
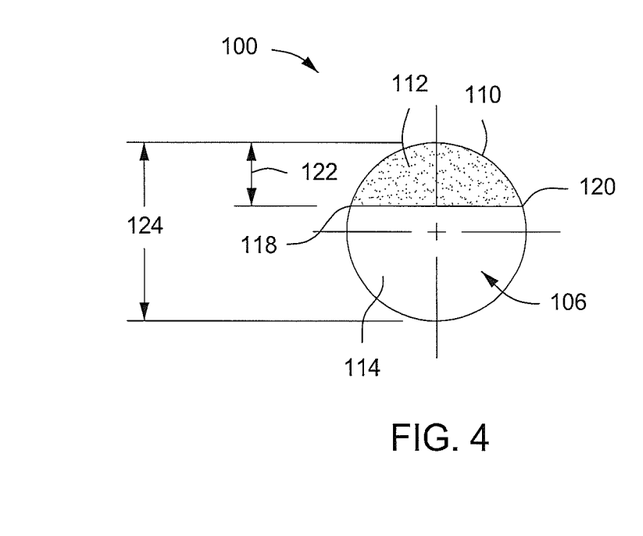
FIG. 4 shows a radial cross section of a filament, according to an aspect of the disclosure.

Referring now to FIGS. 2-4, it will be appreciated that FIG. 2 shows a front view of the filament 100 illustrated in FIG. 1; FIG. 3 shows a radial cross section of the filament 100 in FIG. 2 along section 3-3; and FIG. 4 shows a radial cross section of a filament 100, according to an aspect of the disclosure.

The longitudinal interface 116 may extend through the entire transverse profile 106 of the filament 100, such that the longitudinal interface 116 intersects the outer surface 110 of the filament 100 at a first point 118 and a second point 120. In turn, the first composition 112 may define a portion of the outer surface 110 extending from the first point 118 to the second point 120, and the second composition 114 may define another portion of the outer surface 110 extending from the first point 118 to the second point 120.

According to an aspect of the disclosure, the longitudinal interface 116 is a planar surface extending through the filament 100, such that the longitudinal interface 116 appears as a substantially straight line in radial cross section. Alternatively, it will be appreciated that the longitudinal interface 116 may appear as an arc, an irregular line, or any other line known to persons having ordinary skill in the art.

According to another aspect of the disclosure, a profile of the longitudinal interface 116 in radial cross section remains substantially constant along the longitudinal axis 104 of the filament 100. According to yet another aspect of the disclosure, a profile of the longitudinal interface 116 in radial cross section varies along the longitudinal axis 104 of the filament 100.

As shown in FIG. 3, a radial thickness 122 of the first composition 112 may extend at least half an overall dimension 124 of the filament 100. In one aspect of the disclosure, the transverse profile 106 of the filament 100 is a circular cylindrical profile, and the longitudinal interface 116 lies along a diameter of the circular cylindrical profile of the filament 100. In other words, the first composition may span a sector of transverse profile 106 equal to about 180 degrees.

As shown in FIG. 4, a radial thickness 122 of the first composition 112 may extend less than half an overall dimension 124 of the filament 100. According to an aspect of the disclosure, the radial thickness 122 of the first composition 112 may extend no less than one-quarter of the overall dimension 124 of the filament 100.

Figure 5:
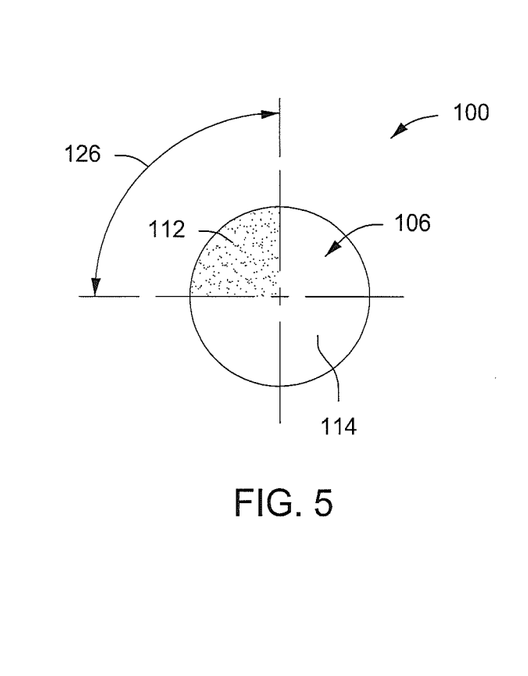
FIG. 5 shows a radial cross section of a filament, according to an aspect of the disclosure.

FIG. 5 shows a radial cross section of a filament 100, according to an aspect of the disclosure. In FIG. 5, the first composition 112 and the second composition 114 contact one another along the longitudinal interface 116. The second composition 114 may compose the balance of the transverse profile 106 of the filament 100. The first composition 112 may compose a sector 126 of the transverse profile 106 of about 90 degrees. However, it will be appreciated that sector 126 could occupy any advantageous extent of the transverse profile 106.

Figure 6:
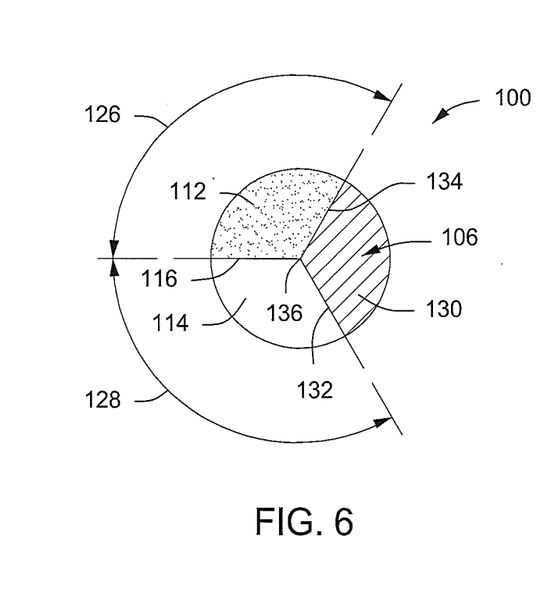
FIG. 6 shows a radial cross section of a filament, according to an aspect of the disclosure.

FIG. 6 shows a transverse profile 106 of a filament 100, according to an aspect of the disclosure. In FIG. 6, the first composition 112 composes a first sector 126 of the transverse profile 106, and the second composition 114 composes a second sector 128 of the transverse profile, where the first composition 112 and the second composition meet at a first longitudinal interface 116. Further according to FIG. 6, a third composition 130 may compose the balance of the transverse profile 106.

According to one aspect of the disclosure, the first sector 126 is about 120 degrees. According to another aspect of the disclosure the second sector 128 is also about 120 degrees. However, it will be appreciated that the first sector 126 and the second sector 128 could occupy any advantageous extent of the transverse profile 106.

The second composition 114 may contact the third composition 130 along a second longitudinal interface 132. Further, the third composition 130 may contact the first composition 112 along a third longitudinal interface 134. The first longitudinal interface 116, the second longitudinal interface 132, and the third longitudinal interface 134 may all intersect along a line through the filament 100 that appears as the point 136 in FIG. 6. Alternatively, the first longitudinal interface 116, the second longitudinal interface 132, and the third longitudinal interface 134 may not all intersect one another at the point 136.

The third composition 130 may differ from the first composition 112 and the second composition 114 by color, molecular weight, polymeric composition, bioactivity, or other suture material characteristic known to persons having ordinary skill in the art. According to one aspect of the disclosure, the third composition 130 differs from the first composition 112 and the second composition 114 only in color.

Figure 7:
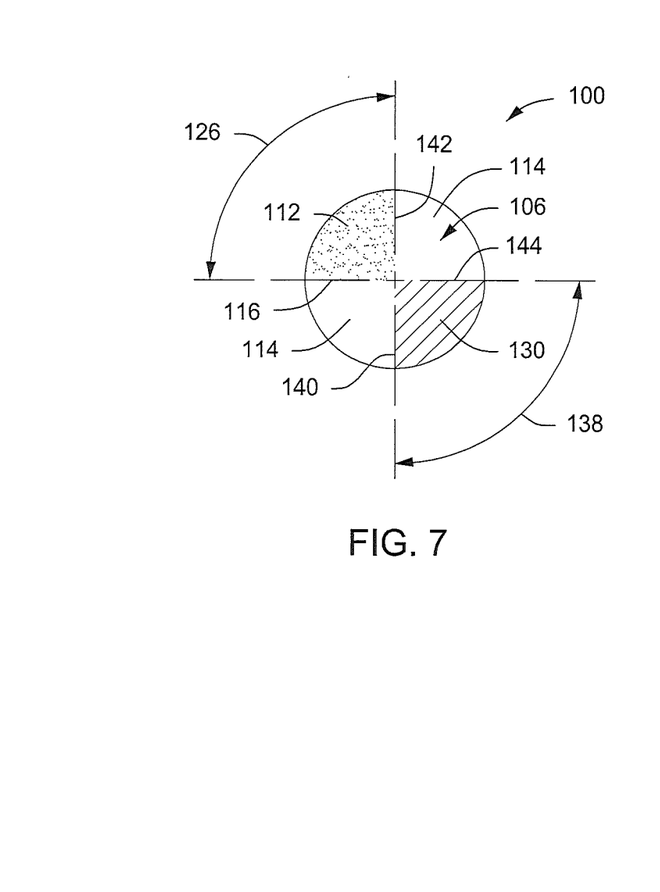
FIG. 7 shows a radial cross section of a filament, according to an aspect of the disclosure.

FIG. 7 shows a transverse profile 106 of a filament 100, according to an aspect of the disclosure. In FIG. 7, the first composition 112 composes a first sector 126 of the transverse profile 106, and the third composition 130 composes a second sector 138 of the transverse profile 106. The first composition 112 and the third composition 130 each contact the second composition 114 along the first longitudinal interface 116 and the second longitudinal interface 140, respectively. Further, the first composition 112 and the third composition 130 each contact the second composition 114 along a third longitudinal interface 142 and a fourth longitudinal interface 144, respectively. Accordingly, the first composition 112 may be separated from the third composition 130 by portions of the second composition 114.

The first sector 126 may extend about 90 degrees, and the second sector 138 may also extend about 90 degrees. Further, the second composition 114 may compose the balance of the transverse profile 106. However, it will be appreciated that the first sector 126 and the second sector 138 may each occupy any advantageous extent of the transverse profile 106.

In FIG. 7, the third composition 130 may differ from the first composition 112 and the second composition 114 by color, molecular weight, polymeric composition, bioactivity, or other suture material characteristic known to persons having ordinary skill in the art. According to one aspect of the disclosure, the third composition 130 differs from the first composition 112 and the second composition 114 only in color. According to another aspect of the disclosure, the first composition 112 and the third composition 130 have the same color, and the color of the first composition 112 and the third composition 130 is different from the color of the second composition 114.

Figure 8:
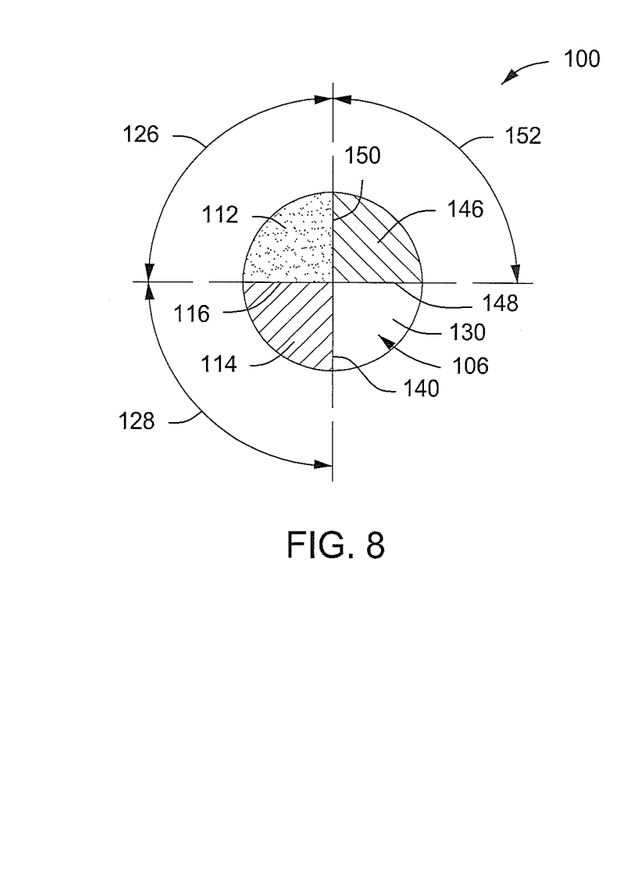
FIG. 8 shows a radial cross section of a filament, according to an aspect of the disclosure.

FIG. 8 shows a transverse profile 106 of a filament 100, according to an aspect of the disclosure. In FIG. 8, the transverse profile 106 of the filament 100 may include the first composition 112, the second composition 114, the third composition 130, and a fourth composition 146. The fourth composition 146 may differ from the first composition 112, the second composition 114, and the third composition 130 by color, molecular weight, polymeric composition, bioactivity, or other suture material characteristic known to persons having ordinary skill in the art. According to one aspect of the disclosure, the fourth composition 146 differs from the first composition 112, the second composition 114, and the third composition 130 only in color.

The first composition 112, the second composition 114, and the fourth composition 146 may extend over a first sector 126, a second sector 128, and a third sector 152, respectively. Further, the third composition 130 may compose the balance of the transverse profile 106. The first sector 126, the second sector 128, and the third sector 152 may each extend over about 90 degrees. However, it will be appreciated that the first sector 126, the second sector 128, and the third sector 152 may each occupy any advantageous extent of the transverse profile 106.

The second composition 114 may contact the third composition 130 at a second longitudinal interface 140, and the third composition 130 may contact the fourth composition 146 at a third longitudinal interface 148. Further, the fourth composition 146 may contact the first composition 112 at a fourth longitudinal interface 150.

Although FIGS. 1-8 show only two to four distinct compositions in the filament 100, it will be appreciated that the filament 100 may include any number of distinct compositions greater than one.

Figure 9:
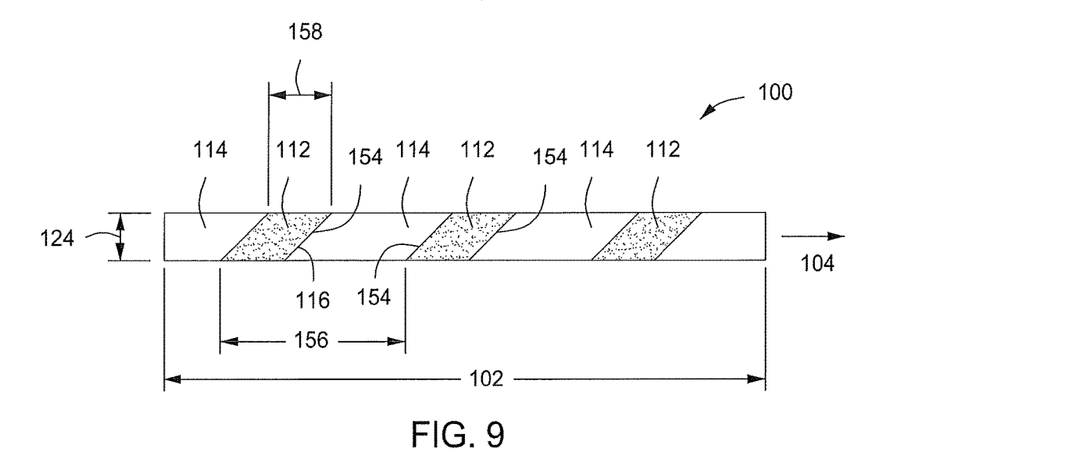
FIG. 9 shows a front view of a filament, according to an aspect of the disclosure.

FIG. 9 shows a front view of a filament 100, according to an aspect of the disclosure. In FIG. 9, a longitudinal interface 116 between the first composition 112 and the second composition 114 is rotated about the longitudinal axis along the length 102 of the filament 100, thereby forming a helical interface 154 between the first composition 112 and the second composition 114. The helical interface 154 may have a pitch 156, indicative of an axial length of the filament 100 per revolution of the helical interface 154. A helical structure of the first composition 112 may have a longitudinal width 158 along the longitudinal axis 104.

Figure 10:
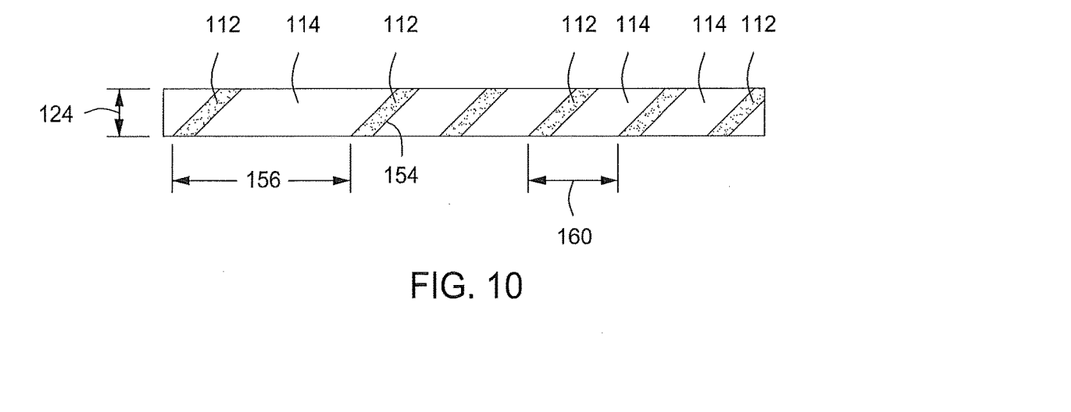
FIG. 10 shows a front view of a filament, according to an aspect of the disclosure.

FIG. 10 shows a front view of a filament 100, according to an aspect of the disclosure. In FIG. 10, similar to FIG. 9, a first composition 112 and a second composition 114 form a helical interface 154. However, in FIG. 10 the helical interface 154 has a first pitch 156 over a first axial length of the filament 100 and has a second pitch 160 over a second axial length of the filament 100. The pitch of the helical interface 154 may be varied along the longitudinal axis 104 of the filament 100 continuously or in discreet steps. Likewise, a filament 100 may include a portion with a flat planar longitudinal interface 116 over a first axial length (see FIG. 1, for example), with no twist about the longitudinal axis 104, and have another portion with a helical interface 154 over a second axial length.

Although FIGS. 9 and 10 show only a first composition 112 and a second composition 114, it will be appreciated that a filament having a transverse profile 106 with any number of distinct compositions greater than one may be twisted about the longitudinal axis 104 of the filament 100 to form any number of distinct helical structures greater than one. Indeed, it will be appreciated that many variations and permutations of the above-described structures are contemplated to be within the scope of the present disclosure.

Figure 11:
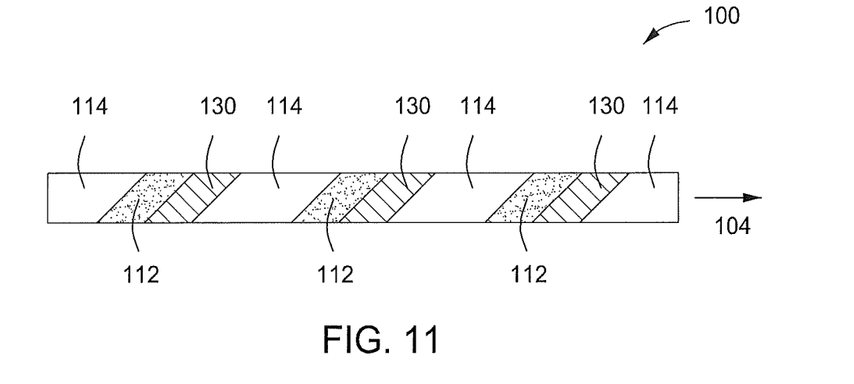
FIG. 11 shows a front view of a filament, according to an aspect of the disclosure.

FIG. 11 shows a front view of a filament 100, according to an aspect of the disclosure. The filament 100 includes helical interfaces between the first composition 112, the second composition 114, and the third composition 130, which may result from helical twisting of the transverse profile 106 shown in FIG. 6 about the longitudinal axis 104, for example.

Figure 12:
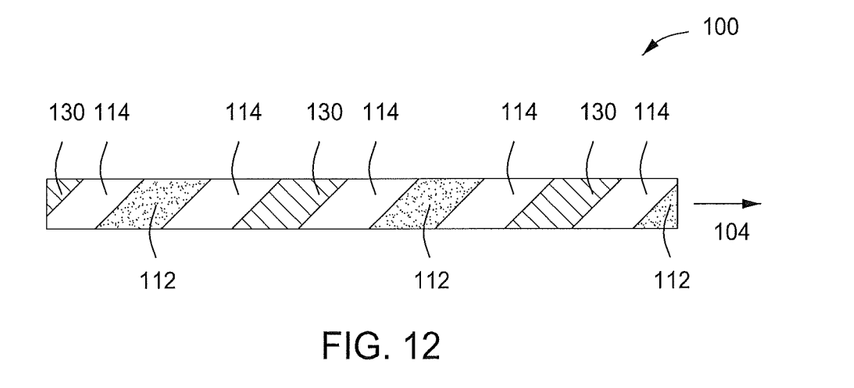
FIG. 12 shows a front view of a filament, according to an aspect of the disclosure.

FIG. 12 shows a front view of a filament 100, according to an aspect of the disclosure. The filament 100 includes helical interfaces between the first composition 112, the second composition 114, and the third composition 130, which may result from helical twisting of the transverse profile 106 shown in FIG. 7 about the longitudinal axis 104, for example. As discussed previously, the color of the first composition 112 may be the same as or different from the color of the third composition 130.

Figure 13:
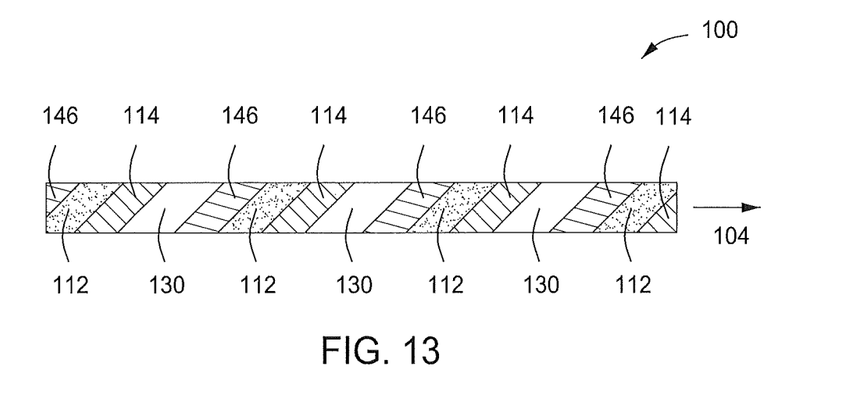
FIG. 13 shows a front view of a filament, according to an aspect of the disclosure.

FIG. 13 shows a front view of a filament 100, according to an aspect of the disclosure. The filament 100 includes helical interfaces between the first composition 112, the second composition 114, the third composition 130, and the fourth composition 146, which may result from helical twisting of the transverse profile 106 shown in FIG. 8 about the longitudinal axis 104, for example.

Figure 14:
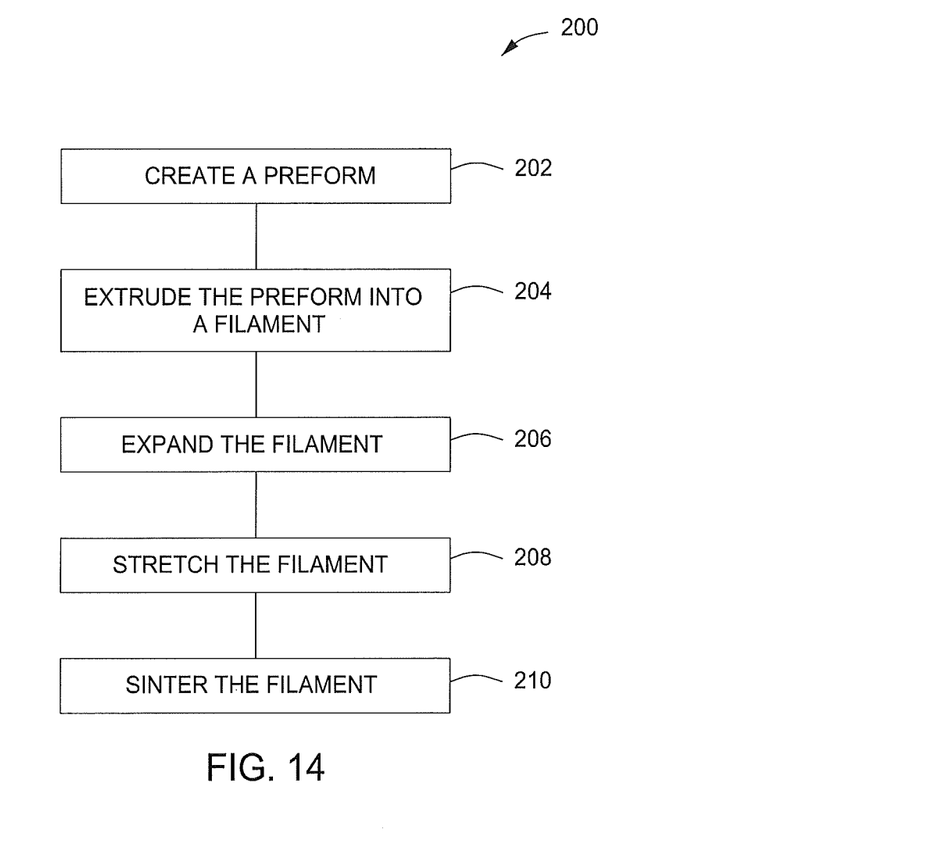
FIG. 14 presents a flowchart for a method of making a filament, according to an aspect of the disclosure.

FIG. 14 presents a flowchart for a method of making a filament 200, according to an aspect of the disclosure. A preform is created in step 202; the preform is extruded to form a filament 100 in step 204; the filament 100 is expanded in step 206; the filament is stretched in step 208; and the filament is sintered in step 210.

Figure 15:
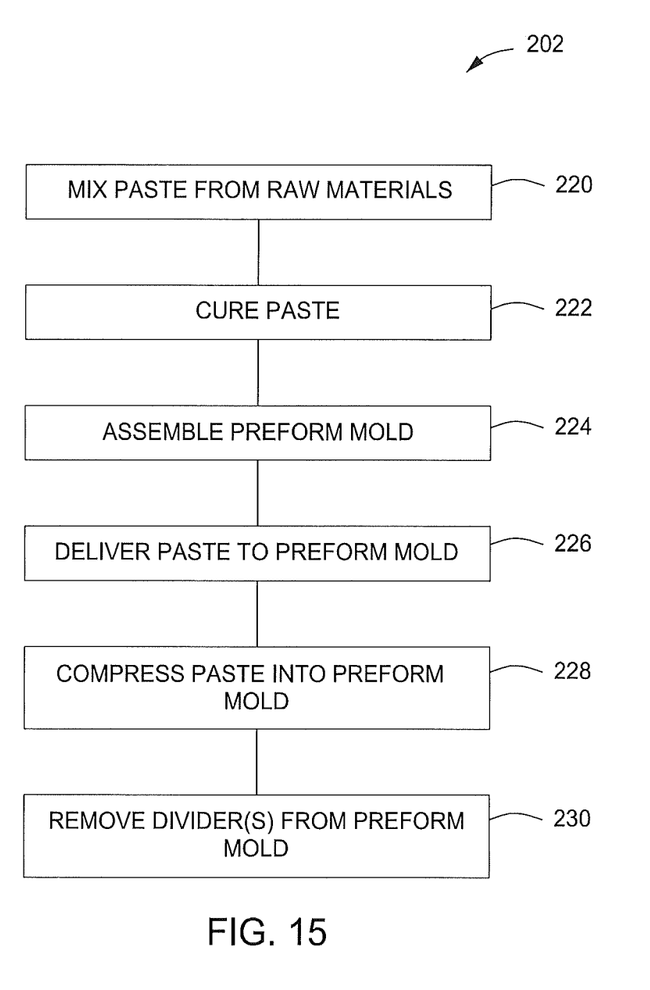
FIG. 15 presents a flowchart for the step of creating a preform, according to an aspect of the disclosure.

FIG. 15 presents a flowchart for the step of creating a preform 202, according to an aspect of the disclosure. In step 220, raw materials are mixed into a paste. The raw materials may include a PTFE resin, a lubricant, a colorant, a bioactive agent, or other suture material additive known to persons having ordinary skill in the art.

The PTFE resin may have a high molecular weight, for example, a molecular weight greater than 2,000,000, and in some embodiments greater than 7,000,000. Non-limiting examples of PTFE resins that may be used according to aspects of the disclosure include Daikin F131, Daikin F104U, Daikin F107, Daikin F201, Daikin F205, or other similar PTFE resins known to persons having ordinary skill in the art. Further, the PTFE resins may be supplied in a powder form for forming the paste in step 220. Some metrics that may be relevant to selecting a particular PTFE resin include material quality at extrusion and strength after drawing.

Examples of the lubricant that could be used in forming the paste in step 220 include isopar-E, isopar-H, isopar-M, kerosene, naphtha, petroleum ether, or other similar hydrocarbon liquid known to persons having ordinary skill in the art. The lubricant mixed with the PTFE resin may facilitate extrusion during the step 204. It will be appreciated that a plurality of paste batches may be formed according to step 220, where each batch includes a different colorant additive.

According to an aspect of the disclosure, the paste formed in step 220 includes PTFE resin powder mixed with about 12 to 20% lubricant by weight. According to another aspect of the disclosure, the paste formed in step 220 includes PTFE resin powder mixed with about 15% lubricant by weight. According to yet another aspect of the disclosure, the paste formed in step 220 includes Daikin F-131 PTFE resin powder mixed with about 15% isopar by weight. However, it will be appreciated that other paste compositions may be used.

The paste raw materials may be mixed in a mixer for about ten to twenty minutes, or until the paste raw materials are thoroughly mixed. A temperature of the paste raw materials may be advantageously controlled between about 50 degrees Fahrenheit and about 60 degrees Fahrenheit during the mixing process to prevent damage to the resin powder.

Next, in step 222 the paste is cured. The paste is cured at a temperature and time duration to ensure the lubricant fully migrates into the paste powder. According to an aspect of the disclosure, the paste is cured for not less than twenty-four hours. According to another aspect of the disclosure, the past is cured at a temperature ranging from about 68 degrees Fahrenheit to about 78 degrees Fahrenheit.

In step 224, a preform mold is assembled. The preform mold may include an outer tube with dividers disposed within the tube. The tube and dividers may be fabricated from stainless steel or other similar material known to be compatible with the paste mixture formed in step 220.

In step 226, paste is delivered into the preform mold. The dividers within the mold tube may define discrete volumes within the mold that are configured to accept different compositions of paste. For example a divider having a wedge shape may be used to separate the first composition 112 from the second composition 114 to compose a preform transverse profile such as that shown in FIG. 5, such that the divider lies at the longitudinal interface 116 between the two compositions 112, 114. Similarly an X-shaped divider may be used to separate the first composition 112, the second composition 114, the third composition 130, and the fourth composition 146 to compose a preform transverse profile such as that shown in FIG. 8. Alternatively, the preform mold may not include any dividers when the preform is composed of only one paste composition. It will be appreciated that a wide variety of divider configurations may be used to compose preform structures including any number of paste compositions arranged in a variety of spatial configurations.

After delivering the cured paste to the preform mold, the dividers may be removed from the preform in step 228. Then in step 230, the paste within the mold may be compressed in a preform machine According to an aspect of the disclosure, the preform is compressed during step 230 at a pressure ranging from about 150 psig to about 190 psig.

Figure 16:
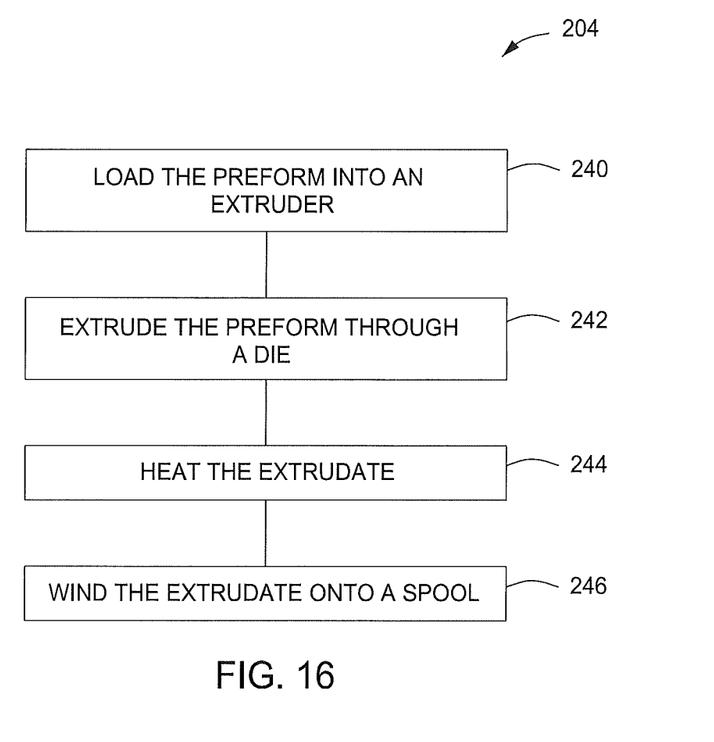
FIG. 16 presents a flowchart for the step of extruding the preform into a filament, according to an aspect of the disclosure.

FIG. 16 presents a flowchart for the step of extruding the preform into a filament 204, according to an aspect of the disclosure. In step 240, the preform is loaded into an extruder. Next, in step 242, the preform is extruded through a sizing die by applying a pressure to the preform. Pressure may be applied to the preform via a hydraulic ram, or any other means for applying pressure to a paste known to persons having ordinary skill in the art. According to an aspect of the disclosure, the pressure applied to the preform during step 242 ranges from about 200 psig to about 400 psig. The extrudate from step 242 may form a green PTFE filament having a transverse profile 106 that is approximately a scaled version of a transverse profile of the preform.

In step 246, an end of the extrudate, downstream of the sizing die, may be coupled to a spool, where the spool is driven to rotate a predetermined speed to roll the green PTFE filament onto the spool. Between the extruder and the spool, the extrudate may pass through a heater, as shown in step 244. The heating step 244 may diffuse a portion of the lubricant from the extrudate. According to one aspect of the disclosure, a temperature within the heater during step 244 is not greater than about 500 degrees Fahrenheit. According to another aspect of the disclosure, a temperature within the heater during step 244 is about 400 degrees Fahrenheit. According to still yet another aspect of the disclosure, the extrudate does not undergo significant sintering during the heating step 244. It will be appreciated that a residence time of the extrudate through the heater during step 244 may be varied based on a length of the heater and a speed of the extrudate traveling through the heater.

During the winding step 246, the end of the extrudate coupled to the spool may be rotated substantially about a longitudinal axis of the extrudate extending from the spool, thereby imparting a helical twist to the extrudate as shown in any one of FIGS. 9-13, for example. According to an aspect of the disclosure, the extrudate may be rolled onto the spool while simultaneously rotating the spool substantially about the longitudinal axis of the extrudate extending from the spool.

Figure 17:
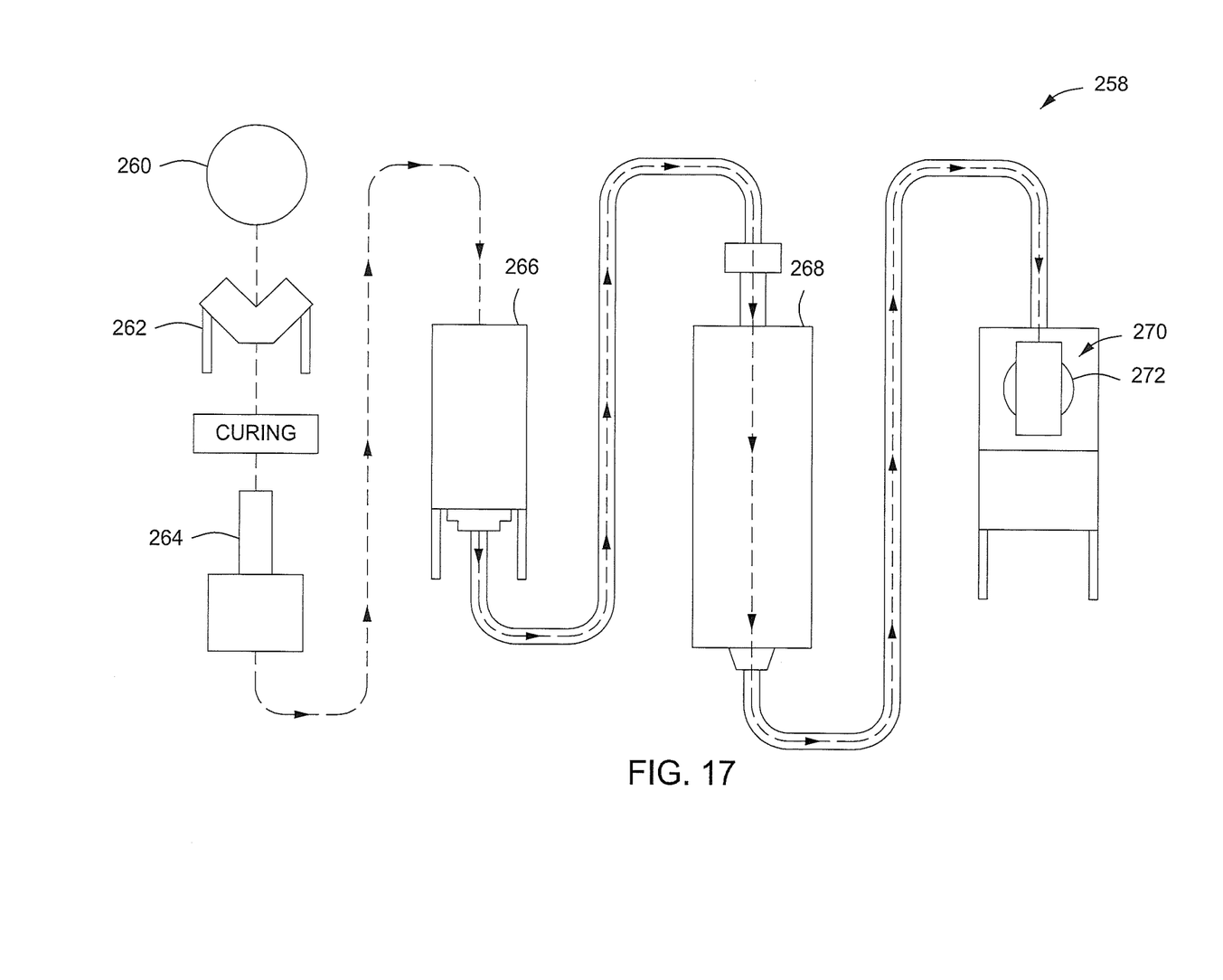
FIG. 17 shows a schematic process map for the steps of creating the preform and extruding the preform into a filament, according to an aspect of the disclosure.

FIG. 17 shows a schematic of a process map for the steps of creating the preform 202 and extruding the preform into a filament 204. Raw materials from a raw material supply 260 are delivered to a mixer 262. Paste from the mixer 262 is delivered to the preform mold 264. The preform is transferred from the preform mold 264 into the extruder 266. Then, the extrudate or green PTFE monofilament leaving the extruder 266 is heated in the heater 268 and wound onto a spool 272 on the winder 270.

Referring now to FIG. 14, the green filament or extrudate may be drawn from the spool and expanded according to step 206. The expansion of the green filament in step 206 may be achieved by drawing the green filament over a heated plate such that the density of the green filament decreases from a first density of about 1.4 to about 1.8 g/cc to a second density of about 0.5 to about 1.4 g/cc. According to an aspect of the disclosure, the heated plate temperature ranges from about 545 degrees Fahrenheit to about 555 degrees Fahrenheit. According to another aspect of the disclosure, the heated plate temperature is about 550 degrees Fahrenheit. According to another aspect of the disclosure, during expansion, the green filament may be exposed to an environment having a temperature range of about 520 degrees Fahrenheit to about 800 degrees Fahrenheit. In some aspects, the temperature of the environment may be about 780 degrees Fahrenheit. According to an aspect of the disclosure, the expanding, stretching and sintering steps can be done in a continuous process, or in other words, the filament may be first subjected to the first temperature, then without delay, subjected to the second temperature. Thus the expanding, stretching and sintering steps are done in a continuous process without stopping or breaks in the process.

According to an aspect of the disclosure, a residence time of the green filament in contact with the heated plate ranges from about 0.1 to about 0.5 seconds. According to another aspect of the disclosure, the heated plate has a length in the direction of travel of the green filament of about 3 inches.

Different from expansion of untwisted green filaments, it will be appreciated that green filaments that embody a helical twist may simultaneously and advantageously experience expansion in multiple directions during the expansion step 206.

In step 208 the green filament is stretched to reduce a transverse dimension of the green filament while maintaining a transverse profile of the filament. According to an aspect of the disclosure, a density of the green monofilament is increased to about 0.8 to about 1.5 g/cc during the stretching step 208. Alternatively, a transverse dimension of the green monofilament may be reduced during the stretching step 208 while maintaining a substantially constant density.

According to another aspect of the disclosure, the green monofilament experiences a stretch ratio ranging from about 5 to about 50 during the stretching step 208. It will be appreciated that the stretching step 208 could include a plurality of stretching steps performed in series on the same green monofilament.

Roundness of the green filament may be maintained through the stretching step 208 by using multiple passes from one godet to another godet within one draw stand to hold the green monofilament in place without using nip rolls. Further, orienting the green filament in a vertical direction, with gravity, may also promote preservation of the green filament shape through the stretching step 208.

According to some aspects of the disclosure, the expansion step 206 and the stretching step 208 can occur simultaneously or nearly simultaneously. According to other aspects of this disclosure the expansion step 206 and the stretching step 208 need not be done simultaneously or nearly simultaneously and may be done in any order.

In step 210, the green filament is sintered. According to one aspect of the disclosure, the sintering step 210 includes stretching the green filament while exposing the green filament to an environmental temperature greater than about 700 degrees Fahrenheit. It will be appreciated that various combinations of sintering temperatures and residence times at the sintering temperature may be employed to effect the desired level of filament sintering. For example, the same degree of sintering may be achieved by lower temperature with longer residence times, or higher temperatures with shorter residence times.

According to an aspect of the disclosure, the final sintered filament has a tensile strength not less than about 100,000 psi. According to another aspect of the disclosure, the final sintered filament has a density between about 0.8 and about 1.5 g/cc.

The present disclosure is applicable to filaments in general and to a filament for use as a surgical suture. Aspects of the disclosure provide a high-strength, expanded PTFE monofilament suture to users, which may include medical equipment developers or end users. The monofilament sutures may provide enhanced visual recognition properties by incorporating one or more pigment additives into the monofilament sutures. The pigment additives may be distributed throughout the suture material, or may be advantageously isolated to localized areas of the suture material to effect color patterns, including unique spiral patterns, for example. Further, radiopaque additives may be incorporated into monofilament sutures so that the sutures may be seen in X-ray images or other fluoroscopy images.

Tensile strength and visual recognition are important properties of a suture. Although conventional approaches for making expanded PTFE sutures may provide sufficient handling and abrasion resistance, Applicants identified that the conventional approaches may provide low tensile strength and may pose difficulty distinguishing the natural white color of PTFE against light or white backgrounds. In turn, Applicants identified improvements to suture tensile strength in combination with pigment additives that could improve the marketability of sutures so produced.

The colors and/or patterns incorporated in to the suture can be used to identify a suture characteristic, such as a cross sectional dimension of the suture such as a diameter or the presence or absence of other additives such as bioactive additives. Further, the colors incorporated into the suture may help users distinguish the suture against a white or light colored background, where a plain white PTFE suture would be difficult to see. Moreover, it will be appreciated that enhanced visibility of the suture material may benefit knot tying procedures.

It will be appreciated that the high-strength and/or colored expanded PTFE filament could be used alone as a monofilament suture, or alternatively, combined in a plurality of fibers as a braided suture. For example, the strength and lubricity of the expanded PTFE filament could be combined with ultra-high molecular weight polyethylene (UHMWPE) fibers to create a braid that has high strength, high lubricity, and improved abrasion resistance. Further, if the expanded PTFE filament has radiopacity, then a braided suture incorporating the expanded PTFE element may be visible during X-ray or fluoroscope imaging.

Combinations of the expanded PTFE filament with other polymer filaments, such as, polyester, polypropylene or other non-absorbable suture materials known to persons having ordinary skill in the art may be advantageous. Alternatively, expanded PTFE filaments could be combined with absorbable (i.e., absorbable by an organism) or slowabsorbing materials to make a composite braided suture that exhibited high strength, but could be at least partly absorbed by an organism, leaving just the expanded PTFE filament when it is desirable to minimize long-term implantation or to minimize the long-term profile of the device and/or repair.

It will be appreciated that the foregoing description provides examples of the disclosed apparatus and method. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

We claim:

1. A method for making an expanded polytetrafluoroethylene (PTFE) monofilament, the method comprising:
    forming a first paste by mixing a PTFE powder with a hydrocarbon solvent, the first paste including less than about 16% of the hydrocarbon solvent by weight;
    curing the first paste by exposing the first paste to a first temperature for a first time duration;
    forming an extrusion preform by pressing the first paste into a form;
    forming a green monofilament by extruding the first paste through a die;
    expanding the green monofilament by exposing the green monofilament to a second temperature for a second time duration, the second time duration occurring after the first time duration;
    stretching the green monofilament substantially along a longitudinal axis of the green monofilament, the stretching the green monofilament occurring after the expanding the green monofilament; and
    sintering the green monofilament after the stretching the green monofilament,
    wherein the expanding, stretching, and sintering are done in a continuous process.

2. The method of claim 1, wherein the forming the first paste includes maintaining a mixture of the PTFE powder and the hydrocarbon solvent at a substantially constant temperature.

3. The method of claim 2, wherein the substantially constant temperature is between about 50 degrees Fahrenheit and about 60 degrees Fahrenheit.

4. The method of claim 1, wherein the first temperature is between about 68 degrees Fahrenheit to about 78 degrees Fahrenheit.

5. The method of claim 4, wherein the first time duration is greater than about 24 hours.

6. The method of claim 1, wherein the extrusion preform is substantially free from mechanical forces acting on a free surface of the extrusion preform during the first time duration.

7. The method of claim 1, wherein the forming the extrusion preform includes imparting a pressure on the first paste between about 150 psi to about 190 psi.

8. The method of claim 1, wherein the forming the extrusion preform includes:
    forming a second paste,
    disposing a divider in the form,
    disposing the second paste in the form such that the second paste is in contact with a first side of the divider, the first side of the divider being opposite a second side of the divider that is in contact with the first paste.

9. The method of claim 8, wherein a color of the first paste is different from a color of the second paste.

10. The method of claim 1, wherein the second temperature ranges from about 520 degrees Fahrenheit to about 800 degrees Fahrenheit.

11. The method of claim 1, wherein expanding the green monofilament includes exposing the green monofilament to an environment at the second temperature.

12. The method of claim 1, wherein the second time duration is between about 0.1 and about 0.5 seconds.

13. The method of claim 1, wherein the sintering the green monofilament includes exposing the green monofilament to a temperature greater than about 700° F. for a third time duration.

14. The method of claim 1, wherein the forming the green monofilament includes imparting a pressure on the first paste between about 200 psi and about 400 psi.

15. The method of claim 8, wherein the forming the green monofilament includes rotating an end of the green monofilament about a longitudinal axis of the green monofilament.

* * * * *